(12) United States Patent
Potenziano et al.

(10) Patent No.: US 11,291,202 B2
(45) Date of Patent: *Apr. 5, 2022

(54) ADMINISTRATION AND MONITORING OF NITRIC OXIDE IN EX VIVO FLUIDS

(71) Applicant: Mallinckrodt Pharmaceuticals Ireland Limited, Dublin (IE)

(72) Inventors: Jim Potenziano, Binghamton, NY (US); Douglas R. Hansell, Easton, PA (US); Jeff Griebel, Arora, CO (US); Eddie Costa, San Diego, CA (US); Lisa Cooper, Upper Black Eddy, PA (US); David William Newman, Lebanon, NJ (US)

(73) Assignee: Mallinckrodt Pharmaceuticals Ireland Limited, Dublin (IE)

( * ) Notice: Subject to any disclaimer, the term of this patent is extended or adjusted under 35 U.S.C. 154(b) by 645 days.

This patent is subject to a terminal disclaimer.

(21) Appl. No.: 15/493,578

(22) Filed: Apr. 21, 2017

(65) Prior Publication Data

US 2017/0215411 A1 Aug. 3, 2017

Related U.S. Application Data

(62) Division of application No. 14/095,621, filed on Dec. 3, 2013, now Pat. No. 9,629,358.

(Continued)

(51) Int. Cl.
*A01N 1/02* (2006.01)
*C12N 5/078* (2010.01)
(Continued)

(52) U.S. Cl.
CPC .......... *A01N 1/0226* (2013.01); *A01N 1/0247* (2013.01); *C12N 5/0641* (2013.01);
(Continued)

(58) Field of Classification Search
CPC ...... A01N 1/0226; A01N 1/0247; A01N 1/02; C12N 5/0641; C12N 5/00; A61M 16/00;
(Continued)

(56) References Cited

U.S. PATENT DOCUMENTS 6,314,956 B1 * 11/2001 Stamler ................ A61K 31/197
128/200.24
2002/0133068 A1 * 9/2002 Huiku ................. A61B 5/14551
600/331

(Continued)

OTHER PUBLICATIONS

Y Ishibe, R Liu, M Ueda, K Mori, N Miura, Role of inhaled nitric oxide in ischaemia-reperfusion injury in the perfused rabbit lung, British Journal of Anaesthesia, vol. 83, Issue 3, 1999, pp. 430-435, ISSN 0007-0912 (Year: 1999).*

(Continued)

*Primary Examiner* — Benjamin R Whatley
*Assistant Examiner* — Curtis A Thompson

(57) ABSTRACT

Described are systems and methods for monitoring administration of nitric oxide (NO) to ex vivo fluids. Examples of such fluids include blood in extracorporeal membrane oxygenation (ECMO) circuits or perfusion fluids used for preserving ex vivo organs prior to transplanting in a recipient. The systems and methods described herein provide for administering nitric oxide to the fluid, monitoring nitric oxide or a nitric oxide marker in the fluid, and adjusting the nitric oxide administration.

12 Claims, 2 Drawing Sheets

Related U.S. Application Data

(60) Provisional application No. 61/787,865, filed on Mar. 15, 2013.

(51) Int. Cl.
| | |
|---|---|
| *A61M 1/14* | (2006.01) |
| *A61L 15/16* | (2006.01) |
| *A61P 43/00* | (2006.01) |
| *A61K 33/06* | (2006.01) |
| *A61K 33/24* | (2019.01) |
| *A61P 9/08* | (2006.01) |
| *A61K 31/74* | (2006.01) |
| *C12N 5/00* | (2006.01) |
| *A61P 9/10* | (2006.01) |
| *A61P 7/02* | (2006.01) |
| *A61M 15/00* | (2006.01) |
| *A61M 16/00* | (2006.01) |

(52) U.S. Cl.
CPC ............... *A01N 1/02* (2013.01); *A61K 31/74* (2013.01); *A61K 33/06* (2013.01); *A61K 33/24* (2013.01); *A61L 15/16* (2013.01); *A61M 1/14* (2013.01); *A61M 15/00* (2013.01); *A61M 16/00* (2013.01); *A61P 7/02* (2018.01); *A61P 9/08* (2018.01); *A61P 9/10* (2018.01); *A61P 43/00* (2018.01); *C12N 5/00* (2013.01)

(58) Field of Classification Search
CPC . A61M 15/00; A61M 1/14; A61P 9/08; A61P 9/10; A61P 7/02; A61P 43/00; A61K 31/74; A61K 33/06; A61K 33/24; A61L 15/16
See application file for complete search history.

(56) References Cited

U.S. PATENT DOCUMENTS

| | | | |
|---|---|---|---|
| 2004/0092805 A1* | 5/2004 | Yarita | A61B 5/14551 600/310 |
| 2004/0122301 A1* | 6/2004 | Kiani | A61B 5/14535 600/336 |
| 2004/0224298 A1* | 11/2004 | Brassil | A01N 1/02 435/1.1 |
| 2009/0197240 A1* | 8/2009 | Fishman | A01N 1/0247 435/1.2 |
| 2011/0136096 A1* | 6/2011 | Hassanein | A01N 1/0226 435/1.2 |
| 2015/0151034 A1* | 6/2015 | Goldstein | A61M 1/3666 424/718 |

OTHER PUBLICATIONS

Hamirani et al., "Methemoglobinemia in a young man", Texas Heart Institute Journal, vol. 35(1), 2008, p. 76-77 (Year: 2008).*

* cited by examiner

ADMINISTRATION AND MONITORING OF NITRIC OXIDE IN EX VIVO FLUIDS

CROSS-REFERENCE TO RELATED APPLICATIONS

This application is a divisional of U.S. patent application Ser. No. 14/095,621 titled, "Administration and Monitoring of Nitric Oxide in Ex Vivo Fluids," by Potenziano et al., that was filed on Dec. 3, 2013. U.S. Ser. No. 14/095,621 claims the benefit under 35 U.S.C. § 119(e) to U.S. Provisional Application No. 61/787,865, filed Mar. 15, 2013. The entire contents of U.S. Ser. No. 14/095,621 and U.S. 61/787,865 are incorporated herein by reference in their entirety.

TECHNICAL FIELD

Embodiments of the present invention generally relate to the field of methods and devices for delivering and monitoring nitric oxide.

BACKGROUND

Cells, tissues, organs, and organisms that are deprived of appropriate blood flow undergo ischemic damage due to oxidative stress and eventually die. Traditional methods of reducing ischemic damage involve perfusing affected tissues with oxygen, but this procedure can cause significant tissue damage and can result in serious and/or permanent injury, such as brain damage during stroke or cardiac arrest.

Attempts have been made to reduce ischemia and reperfusion injury by inducing tissues and organs to enter a reduced metabolic state. In the context of living tissues being preserved for transplant or grafting, one common method for reducing their metabolic activity is by immersing tissues or organs in a physiologic fluid, such as saline, and placing them in a cold environment. However, such methods cannot be relied upon for extended periods, and the success of organ transplant and limb reattachments remains inversely related to the time the organ or limb is out of contact with the intact organism.

Separately, oxygen deprivation can also occur in living organisms when the lungs are improperly functioning or not functioning at all. One approach to improving oxygenation in patients is through the use of extracorporeal membrane oxygenation (ECMO), in which venous blood is extracted from the patient, passed through a membrane oxygenator, and then returned to the patient. The ECMO system may include filters or other components which are used to remove blood clots and other biological materials that may need removal before blood is reintroduced into the patient thereby avoiding clogging of the ECMO system, in particular clogging of the membrane oxygenator. There is a need to improve existing ECMO systems and methods to avoid this clogging.

SUMMARY

Embodiments of the present invention provide methods and systems for administering NO-containing gas directly to ex vivo fluid, as well as monitoring the nitric oxide and/or a nitric oxide marker in the fluid. The methods and systems described herein may be utilized for a variety of purposes, including prevention and treatment of ischemia reperfusion injury and for preventing blood clots in an ECMO circuit. The NO may be administered to various biological materials, including cells, tissues, organs, organisms, and animals, including humans and other mammals.

Although the methods and systems described herein have many applications, in particular it is believed that the administration of nitric oxide and the monitoring thereof are beneficial in the context of ECMO circuits and/or the preservation of organs and other biological material for transplantation. With respect to ECMO, in which a patient blood's is oxygenated ex vivo, NO is added to the ECMO circuit and nitric oxide or a nitric oxide marker is monitored and adjusted accordingly. Without wishing to be bound by any particular theory, it is believed that NO administration to blood in an ECMO circuit will reduce platelet activation in the blood, and thus help prevent clogging in the ECMO circuit. Accordingly, NO administration may be used to prevent clogs thereby extending the life of the ECMO circuit. However, excess NO may result in the formation of methemoglobin, which does not bind oxygen, and can lead to methemoglobinemia. As a result, NO administration may be monitored to ensure that the methemoglobin or other nitric oxide marker does not rise above or below a certain safety threshold.

With respect to organ and biological material transplant, an organ is removed from a donor and is appropriately preserved for implantation into a recipient. Biological materials, including cells, tissues and organs, that are used for transplantation require effective ex vivo preservation from the moment the organ or other biological material is retrieved to the time of transplantation. Organ transplantation includes many methods that may be used individually or in combination. In one or more methods, nitric oxide is administered to perfusion fluid and nitric oxide or a nitric oxide marker is monitored in the perfusion fluid and the amount of NO being administered is adjusted if necessary in order to meet or maintain an appropriate amount of NO. It is believed that nitric oxide administration to perfusion fluids and monitoring thereof can extend organ donor pool and increase viability of donated organs. NO may be used as a preconditioning agent to limit organ damage from ischemia reperfusion injury. NO is expected to help with organ preservation by reducing the warm ischemia "hit" which occurs when blood is re-perfused to an organ post-transplant. While not wishing to be bound by any particular theory, it is believed that this reduction in warm ischemia hit may occur by multiple mechanisms, including reduction in oxidative stress and/or preservation of key cellular function.

Furthermore, nitric oxide administration may also reduce microcirculation alterations that can occur after removing an organ for transplant and/or during/following ECMO. For example, after an organ is removed, the microcirculation of the organ can undergo restructuring, which can greatly affect perfusion through the organ. The more restructuring that occurs, the poorer the prognosis for the organ transplant. NO may be used to treat and/or prevent such microcirculation alteration, such as by administering NO, monitoring microcirculation and adjusting the NO administration in response to microcirculation alterations.

Accordingly, one aspect of the present invention is directed to a method of monitoring nitric oxide administration. In one or more embodiments, this method comprises administering nitric oxide to an ex vivo fluid, monitoring nitric oxide or a nitric oxide marker in the ex vivo fluid and adjusting the nitric oxide administration based on the monitoring of the nitric oxide or nitric oxide marker. The ex vivo fluid may contain components such as red blood cells, etc. Administrating nitric oxide to the ex vivo fluid may comprise contacting the ex vivo fluid with a gas comprising a nitric oxide concentration in the range from 1 ppm to 300 ppm. The ex vivo fluid can be contacted with cells after administrating nitric oxide to the fluid.

In one or more embodiments, the ex vivo fluid comprises one or more of blood or perfusion fluid. The ex vivo fluid may comprise blood that is recirculated in an extracorporeal membrane oxygenation (ECMO) circuit and the cells may comprise in vivo cells. The ex vivo fluid may comprise perfusion fluid and the cells may comprise ex vivo organ cells.

The ex vivo fluid may also be oxygenated one or more of before administrating nitric oxide to the ex vivo fluid or after administrating nitric oxide to the ex vivo fluid. The nitric oxide or nitric oxide marker may be monitored one or more of before oxygenating the ex vivo fluid, after oxygenating the ex vivo fluid and before administering nitric oxide to the ex vivo fluid, after administering nitric oxide to the ex vivo fluid and before contacting the cells with the ex vivo fluid, or after contacting the cells with the ex vivo fluid.

The nitric oxide marker may be monitored continuously or intermittently and the nitric oxide administration may be adjusted continuously or intermittently. In one or more embodiments, monitoring the nitric oxide marker comprises one or more of monitoring methemoglobin in the ex vivo fluid or monitoring $NO_x$ in the ex vivo fluid. In one or more embodiments, adjusting the nitric oxide administration comprises adjusting one or more of the nitric oxide concentration or the flow of the gas comprising nitric oxide.

Another aspect of the present invention relates to a method of monitoring nitric oxide administration during extracorporeal membrane oxygenation (ECMO). In one or more embodiments, this method comprises administering nitric oxide to ex vivo blood in an ECMO circuit by contacting the ex vivo blood with a gas comprising a nitric oxide concentration in the range from 1 ppm to 50 ppm, monitoring one or more of (1) a pressure drop in the ECMO circuit to determine if the pressure drop is above a pressure drop threshold or (2) nitric oxide or a nitric oxide marker in the ex vivo blood to determine if the nitric oxide or nitric oxide marker is below or above a nitric oxide threshold, and adjusting the nitric oxide administration based on one or more of the monitoring of the pressure drop or the monitoring of the nitric oxide or nitric oxide marker. The nitric oxide administration may be increased if the pressure drop is above the pressure drop threshold and the nitric oxide administration may be decreased if the nitric oxide or nitric oxide marker is above the nitric oxide threshold.

In one or more embodiments, the pressure drop threshold is in the range from 1% to 30% of the maximum pressure in the ex vivo circuit.

In one or more embodiments, adjusting the nitric oxide administration comprises adjusting one or more of the nitric oxide concentration or the flow of the gas comprising nitric oxide.

In one or more embodiments, monitoring the nitric oxide marker comprises one or more of monitoring methemoglobin in the ex vivo blood or monitoring $NO_x$ in the ex vivo blood. Monitoring the nitric oxide marker may comprise monitoring methemoglobin and the nitric oxide threshold may be in the range from 1% to 15% methemoglobin. In some embodiments, the nitric oxide marker is monitored via one or more of pulse oximetry and optical measurement.

Another aspect of the present invention pertains to a method of monitoring nitric oxide administration to an ex vivo fluid for biological material preservation. In one or more embodiments, this method comprises administering nitric oxide to an oxygenated ex vivo fluid comprising red blood cells by contacting the ex vivo fluid with a gas comprising a nitric oxide concentration in the range from 20 ppm to 200 ppm, monitoring nitric oxide or a nitric oxide marker in the ex vivo fluid, and adjusting the nitric oxide administration based on the monitoring of the nitric oxide or nitric oxide marker. The biological material may comprise one or more of isolated cells, tissue, a partial organ or a complete organ. In one or more embodiments, the organ comprises one or more of a heart, lung, kidney, liver, pancreas, eye, bone, skin, heart valve, bowel, tendon, ligament or vein.

In one or more embodiments, monitoring the nitric oxide marker comprises one or more of monitoring methemoglobin in the ex vivo blood or monitoring $NO_x$ in the ex vivo blood. Monitoring the nitric oxide marker may comprise monitoring methemoglobin and the nitric oxide threshold may be in the range from 1 to 50% methemoglobin.

In one or more embodiments, adjusting the nitric oxide administration comprises adjusting one or more of the nitric oxide concentration or the flow of the gas comprising nitric oxide Also provided is a system for delivering and monitoring nitric oxide. In one or more embodiments, the system comprises a nitric oxide delivery device for administering nitric oxide to an ex vivo fluid and a monitoring device for monitoring nitric oxide or a nitric oxide marker in the ex vivo fluid. The monitoring device may be in communication with the nitric oxide delivery device, and the nitric oxide delivery device may adjust the nitric oxide administration based on the monitoring of the nitric oxide or nitric oxide marker. The monitoring device may be part or integrated with the nitric oxide delivery device, or it may be a separate component from the nitric oxide delivery device.

In one or more embodiments, administrating nitric oxide comprises contacting the ex vivo fluid with a gas comprising a nitric oxide concentration in the range from 1 ppm to 300 ppm.

The monitoring device may comprise any appropriate measurement device, including one or more of a pulse oximeter or an optical measurement device.

In one or more embodiments, the nitric oxide delivery device is in communication with a first pressure sensor and a second pressure sensor in an extracorporeal oxygenation (ECMO) circuit that provide a first pressure reading and a second pressure reading, respectively, and the nitric oxide delivery device adjusts the nitric oxide administration based on a differential between the first pressure reading and the second pressure reading. In some embodiments, the nitric oxide delivery device increases the nitric oxide administration if the differential between the first pressure reading and the second pressure reading is above 1% to 30% of the first pressure reading.

In one or more embodiments, the nitric oxide delivery device adjusts one or more of the nitric oxide concentration or the flow of gas comprising nitric oxide.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION OF THE INVENTION

Figure 1:
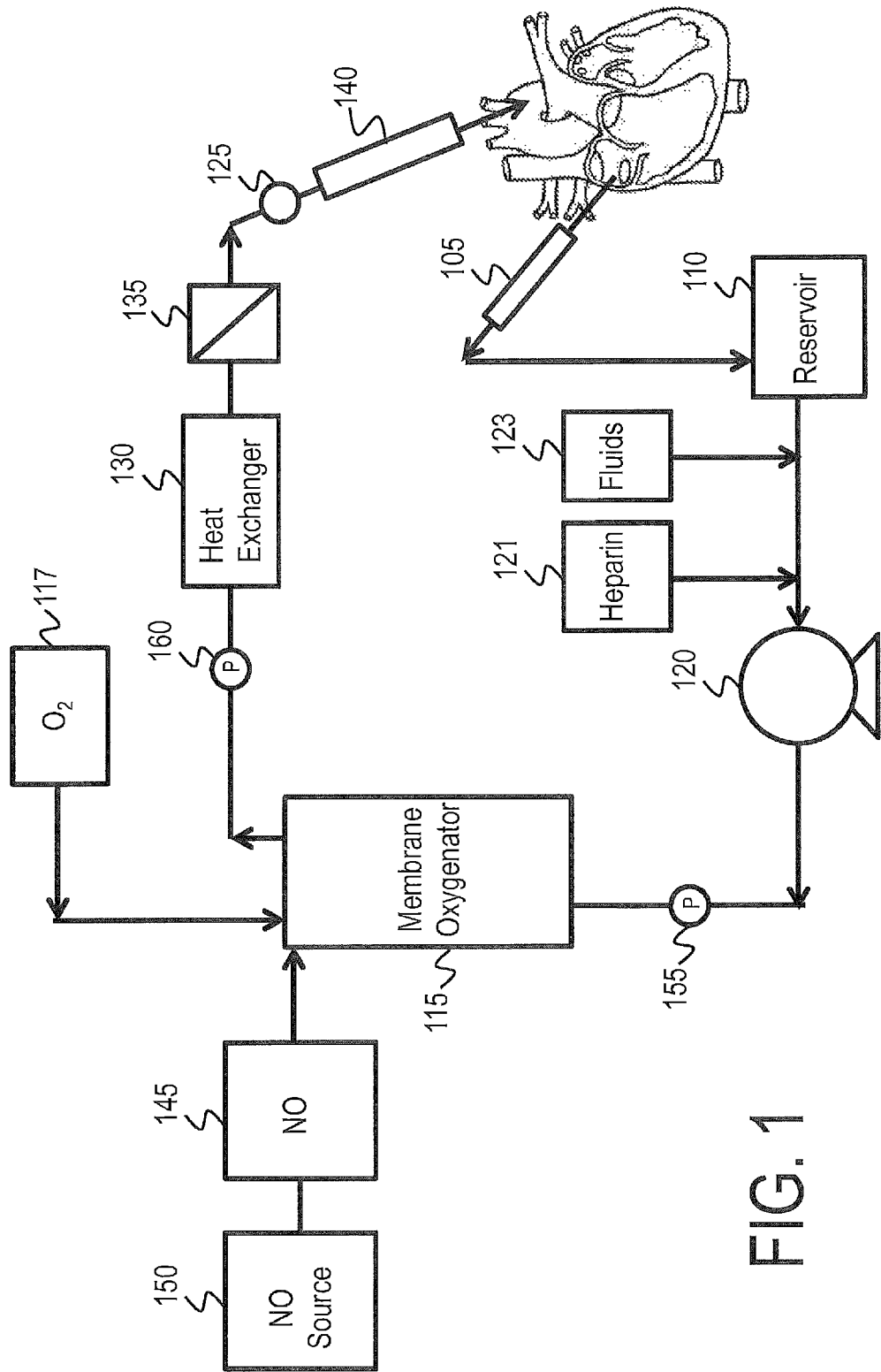
FIG. 1 illustrates an exemplary ECMO circuit that can be used in accordance with one or more embodiments of the invention.

As used in the specification and appended claims, unless specified to the contrary, the following terms have the meaning indicated:

The term "biological material" refers to any living biological material, including cells, tissues, organs, and/or organisms. It is contemplated that the methods of the present invention may be practiced on a part of an organism (such as in cells, in tissue, and/or in one or more organs), or on the whole organism. The term "in vivo biological material" refers to biological material that is in vivo, i.e., still within or attached to an organism.

"Ex vivo fluid" refers to any fluid outside of a living organism. The fluid may provide blood and/or components of blood or other components that are beneficial for a biological material. For example, such fluids can contain red blood cells for carrying oxygen to the biological material. Exemplary ex vivo fluids include, but are not limited to, perfusion fluid and ex vivo blood. Ex vivo fluid may be taken from a living organism (such as a mammal) or can be synthetic.

"Delivery concentration" refers to the concentration of NO gas in a composition of NO-containing gas for medical use which is delivered to an ex vivo fluid. In addition to NO gas, such compositions for medical use may further comprise an inert diluent gas. It is to be understood that the delivery concentration will be diluted upon contact with the ex vivo fluid, where it is mixed and distributed to the target biological material.

"Nitric oxide marker" refers to a direct or indirect indicator of nitric oxide concentration in a fluid. For example, nitric oxide markers include, among others, methemoglobin and NO (i.e. NO, nitrite ions ($NO_2^-$), nitrate ions ($NO_3^-$), etc.).

The term "perfusion fluid" refers to any fluid used in the preservation of ex vivo cells, tissue or organs. Often, perfusion fluids will have compositions similar to blood or contain components found in blood such as red bloods cells, salts, preservatives, etc. Perfusion fluids are often sterile and isotonic. The composition of the perfusion fluid may vary between organs.

"Therapeutically effective amount" refers to that amount of NO gas that, when administered to a subject, organ and/or device, is sufficient to effect treatment as defined herein. The amount of NO which constitutes a "therapeutically effective amount" will vary depending on a variety of factors, but may be determined by one of ordinary skill in the art.

"Treating" or "treatment" as used herein covers the treatment of the disease or condition of interest in a subject or organ of a subject, or the blood of a subject, having the disease or condition of interest, and includes: (i) preventing the disease or condition from occurring in the subject, (ii) inhibiting the disease or condition, i.e., arresting its progression; (iii) relieving the disease or condition, i.e., causing regression of the disease or condition; or (iv) relieving the symptoms resulting from the disease or condition. As used herein, the terms "disease," "disorder," and "condition" may be used interchangeably.

Aspects of the current invention relate to a method of monitoring nitric oxide (NO) administration comprising administering NO-containing gas to an ex vivo fluid, such as one that contains red blood cells, and monitoring nitric oxide or a nitric oxide marker in the fluid. The fluid may be oxygenated before and/or after administrating the nitric oxide. After administering nitric oxide to the fluid and optionally oxygenating the fluid (either before and/or after NO administration), the fluid is transported to and contacted with cells in a biological material. These cells may be isolated cells, tissue, partial organs, complete organs, or may be within a living organism such as a mammal.

The NO-containing gas comprises nitric oxide and optionally a carrier gas such as nitrogen, helium and/or air. The NO-containing gas may be provided by any known method, such as from a gas cylinder or chemically generating the NO at or near the place of administration. The NO-containing gas may be at a higher concentration in the cylinder or other gas source and be diluted to a delivery concentration prior to use.

Alternatively, a NO donor may be used instead of or in addition to a NO-containing gas. NO donors are known in the art and include compounds such as nitroglycerin and sodium nitroprusside.

In one or more embodiments, the delivery concentration of NO in the NO-containing gas is in the range from 0.1 ppm and 500 ppm. Exemplary delivery concentrations may be in the range from 1 to 300 ppm, in the range from 10 ppm to 200 ppm or in the range from 80 ppm to 160 ppm, such as about 1 ppm, about 2 ppm, about 3 ppm, about 4 ppm, about 5 ppm, about 6 ppm, about 7 ppm, about 8 ppm, about 9 ppm, 10 ppm, about 15 ppm, about 20 ppm, about 25 ppm, about 30 ppm, about 35 ppm, about 40 ppm, about 45 ppm, about 50 ppm, about 60 ppm, about 70 ppm, about 80 ppm, about 90 ppm, about 100 ppm, about 110 ppm, about 120 ppm, about 130 ppm about 140 ppm, about 150 ppm, about 160 ppm, about 170 ppm, about 180 ppm, about 190 ppm or about 200 ppm.

In one or more embodiments, the NO-containing gas is administered continuously, for example by continuously contacting the ex vivo fluid with the NO-containing gas. The NO-containing gas may also be administered as a "pulse" or series of pulses to the ex vivo fluid. Similarly, the oxygen may be administered either continuously or pulsed. NO and oxygen may also be intermittently pulsed.

A device can be used to monitor nitric oxide or a nitric oxide marker in the ex vivo fluid and/or used to monitor in the living organism or cells. Such monitoring may comprise monitoring the methemoglobin and/or $NO_x$ in the ex vivo fluid. These nitric oxide markers may be measured directly through techniques such as pulse oximetry or optical measurement or any other means for measuring or co-relating NO or NO markers either directly or indirectly. For example, another measurement technique involves placing a probe in the ex vivo fluid to measure fluid NO levels and may provide real-time analysis of the ex vivo fluid.

The monitoring device may be part of or integrated into the NO delivery device, or the nitric oxide or nitric oxide marker may be monitored by a component separate from the NO delivery device.

In one or more embodiments, the nitric oxide administration is adjusted based on the monitoring of the nitric oxide or nitric oxide marker. Such adjustment may be manual or automatically implemented by the NO delivery device. The NO delivery system may also provide an alarm based on the monitoring. If the monitoring device is a separate component from the NO delivery device, the monitoring device may transmit the monitoring information to the NO delivery device via any appropriate wired or wireless connection. For example, if the nitric oxide or nitric oxide marker in the fluid is below a certain threshold, NO delivery may be increased until the nitric oxide or nitric oxide marker in the fluid meets the threshold. Similarly, if the nitric oxide or nitric oxide marker in the fluid is above a certain threshold, the amount of NO administered may be decreased.

In one or more embodiments, the nitric oxide or nitric oxide marker is monitored by comparing a measurement of the nitric oxide or nitric oxide marker to a nitric oxide threshold. The nitric oxide threshold may be a safety limitation that ensures that methemoglobinemia does not develop. For example, the nitric oxide threshold may be a methemoglobin level, such as a percentage of methemoglobin relative to the red blood cells. In exemplary embodiments, the nitric oxide threshold is in the range from about 1% to about 15% methemoglobin, or about 3% to about 10% methemoglobin. Accordingly, the nitric oxide administration may be adjusted if the methemoglobin levels meet or exceed an acceptable range, such as ≤3%, ≤4%, ≤5%, ≤6%, ≤7%, ≤8%, ≤9%, ≤10%, ≤11% or ≤12%.

The nitric oxide or nitric oxide marker may be monitored either continuously or intermittently, such as at regular intervals. The nitric oxide administration may also be adjusted continuously or intermittently. The oxygen administration may be administered continuously or intermittently and may be adjusted continuously or intermittently.

The level of $NO_2$ may also be monitored in the ex vivo fluid. $NO_2$ may build up in the fluids due to recirculation of the fluids. If the $NO_2$ concentration rises above a certain threshold, NO delivery device may adjust the NO administration and/or provide an alarm. The $NO_2$ may also be removed through the use of a reducing agent, scrubber, base, or other appropriate means.

In one or more embodiments, the nitric oxide is administered at an initial concentration, and then increased as necessary to obtain the desired effect. For example, the initial nitric oxide concentration may be in the range from 0.05 ppm to 100 ppm or 1 ppm to 50 ppm and then increased incrementally until the desired effect is obtained or a nitric oxide threshold is met. An exemplary nitric oxide administration may begin at an initial concentration of 20 ppm, then increased in increments of 0.1 ppm to 5 ppm until the desired NO effect is obtained, but ensuring that the NO concentration does not exceed 80 ppm and/or that the methemoglobin levels do not meet or exceed about 5%. The initial nitric oxide concentration, increments of nitric oxide increase, maximum nitric oxide concentration and/or threshold for the nitric oxide or nitric oxide marker may be varied depending on the application. It is believed that lower initial nitric oxide concentrations (such as in the range from 1 ppm to 50 ppm) and smaller incremental increases in nitric oxide concentration will enable the nitric oxide delivery device to arrive at the ideal nitric oxide concentration without presenting safety issues. The nitric oxide may also be incrementally decreased if the monitoring indicates that the nitric oxide or nitric oxide marker meets or exceeds the nitric oxide threshold.

Exemplary initial delivery concentrations of NO may be in the range from 0.05 ppm to 300 ppm, in the range from 1 ppm to 50 ppm, or in the range from 5 ppm to 40 ppm, such as about 1 ppm, about 2 ppm, about 3 ppm, about 4 ppm, about 5 ppm, about 6 ppm, about 7 ppm, about 8 ppm, about 9 ppm, 10 ppm, about 15 ppm, about 20 ppm, about 25 ppm, about 30 ppm, about 35 ppm, about 40 ppm, about 45 ppm, about 50 ppm, about 60 ppm, about 70 ppm, about 80 ppm, about 90 ppm, about 100 ppm, about 110 ppm, about 120 ppm, about 130 ppm about 140 ppm, about 150 ppm, about 160 ppm, about 170 ppm, about 180 ppm, about 190 ppm or about 200 ppm. The initial NO concentration may be different between applications. For example, the initial NO concentration may be around 20 ppm for applications such as NO administration in ECMO circuits, and the initial NO concentration may be a higher value such as 80 ppm in applications in which there is less sensitivity to methemoglobin levels (such as NO administration in organ preservation). The initial NO concentrations and incremental adjustments and monitoring may also differ for organ preservation based on the particular organ being treated.

Exemplary increments in NO concentration may be about 1 ppm, about 2 ppm, about 3 ppm, about 4 ppm, about 5 ppm, about 6 ppm, about 7 ppm, about 8 ppm, about 9 ppm, 10 ppm, about 15 ppm, about 20 ppm or about 25. The increments may vary throughout the adjustment of the nitric oxide delivery, i.e. the first increment may be 10 ppm, the second increment may be 5 ppm, and the third increment is 1 ppm.

The NO concentration may also be incrementally adjusted by a certain percentage relative to the last NO concentration. Such incremental percentages can include 5%, 10%, 15%, 20%, 25%, 30%, 35%, 40%, 45%, 50%, 55%, 60%, 65%, 70%, 75%, 80%, 85%, 90%, 95%, 100%, 110%, 125%, 150%, 175% and 200% changes in the NO concentration.

Instead of or in addition to adjusting the NO concentration, the NO administration may be adjusted by any means for adjusting the amount of NO that is delivered to the ex vivo fluid, such as by adjusting the flow rate of NO-containing gas that is delivered to the ex vivo fluid. The flow rate of NO-containing gas may be, for example, 5 mL/min, 10 mL/min, 15 ml/min, 20 mL/min, 25 mL/min, 30 mL/min, 40 mL/min, 50 mL/min, 60 mL/min, 70 mL/min, 80 mL/min, 90 mL/min, 0.1 L/min, 0.15 L/min, 0.2 L/min, 0.25 L/min, 0.3 L/min, 0.35 L/min, 0.4 L/min, 0.45 L/min, 0.5 L/min, 0.55 L/min, 0.6 L/min, 0.65 L/min, 0.7 L/min, 0.75 L/min, 0.8 L/min, 0.85 L/min, 0.9 L/min, 1 L/min, 1.25 L/min, 1.5 L/min, 1.75 L/min, 2 L/min, 2.5 L/min, 3 L/min, 3.5 L/min, 4 L/min, 4.5 L/min, 5 L/min, 5.5 L/min, 6 L/min, 6.5 L/min, 7 L/min, 8 L/min, 9 L/min or 10 L/min. The flow rate may be adjusted in incremental amounts, such as in increments in 5 mL/min, 10 mL/min, 15 mL/min, 20 mL/min, 25 mL/min, 30 mL/min, 40 mL/min, 50 mL/min, 60 mL/min, 70 mL/min, 80 mL/min, 90 mL/min, 0.1 L/min, 0.15 L/min, 0.2 L/min, 0.25 L/min, 0.3 L/min, 0.35 L/min, 0.4 L/min, 0.45 L/min, 0.5 L/min, 0.55 L/min, 0.6 L/min, 0.65 L/min, 0.7 L/min, 0.75 L/min, 0.8 L/min, 0.85 L/min, 0.9 L/min, 1 L/min, 1.25 L/min, 1.5 L/min, 1.75 L/min, 2 L/min, 2.5 L/min, 3 L/min, 3.5 L/min, 4 L/min, 4.5 L/min, 5 L/min, 5.5 L/min, 6 L/min, 6.5 L/min, 7 L/min, 8 L/min, 9 L/min or 10 L/min. The flow rate may also be adjusted by a certain percentage relative to the last flow rate. Such incremental percentages can include 5%, 10%, 15%, 20%, 25%, 30%, 35%, 40%, 45%, 50%, 55%, 60%, 65%, 70%, 75%, 80%, 85%, 90%, 95%, 100%, 110%, 125%, 150%, 175% and 200% changes in the flow rate of the NO-containing gas.

The device for introduction of NO-containing gas into the ex vivo fluid may comprise a container, gas cylinder or receptacle for holding or locally generating the NO-containing gas, referred to as an "NO generator/receptacle". The device for introduction of the NO-containing gas into the ex vivo fluid will typically include a pump, injector or metering device to facilitate delivery of the NO-containing gas into the ex vivo fluid, referred to as an "NO delivery device".

The NO delivery device may include any appropriate components for administering NO to the ex vivo fluid, including flow sensors, valves, flow controllers, processors, safety shut-off valves, purge valves, etc. The NO delivery device may also include components for monitoring the gas that is administered to the fluid, such as gas concentration sensors (e.g. $O_2$, NO and/or $NO_2$ sensors), sampling pumps, etc. The NO delivery device may also include redundant sensors and/or valves and have an automatic backup delivery system in case of failure of the primary NO delivery system. The NO delivery device may also include one or more sensors for feedback control of the NO delivery and/or for independent safety monitoring of NO delivery. The NO delivery device can also provide alarms if any of the monitored parameters meet or exceed a certain level or if other safety issues are present. The NO delivery device may also include fluid flow or pressure sensors that are placed near the NO injection point, or integrated into the NO injection point, so that NO may only be injected when fluid is moving through the system or organ.

The NO delivery device may be portable and light (<10 lbs) so that it does not hinder the transport process and can be able to mount to existing transport boxes. The NO delivery device may run on a battery and have a battery life that meets a certain minimum criteria, such as having a battery life of at least 16 hours. The NO delivery device may also include a backup battery or other power source.

The NO source may include two or more gas cylinders such that continuous NO administration is not interrupted when one of the gas cylinders is replaced.

The NO delivery device may also include an automated pre-use checkout procedure with automatic purge to clear $NO_2$, and on-screen setup instructions. The system may also have on-screen alarm help, and wireless connectivity to communicate with an electronic medical record (EMR) system or a tech support desk for remote troubleshooting. Another safety feature may be the incorporation of sensors and mechanisms to automatically detect fluid or gas leaks.

A device may also be used to monitor the microcirculation of a tissue, organ or organism. The microcirculation monitoring device may measure the partial pressure of carbon dioxide ($PCO_2$) in the desired tissue, organ or organism. The microcirculation monitoring device may be part of or integrated into the NO delivery device, or may be monitored by a component separate from the NO delivery device. The microcirculation may be monitored continuously or intermittently. The NO delivery device may adjust the NO administration in response to changes in the microcirculation. For example, if the microcirculation restructuring increases, the NO dose may be increased. The device may also include at least one redundant microcirculation monitoring sensor that is independent from delivery control, or another monitoring mechanism to ensure patient safety. Such redundant sensors may help prevent overdosing or under-dosing in the event of a microcirculation sensor failure.

In certain embodiments, methods, compositions, and devices of the present invention are used to treat or prevent any of a variety of diseases and disorders that benefit from treatment with nitric oxide. In particular embodiments, the methods of the present invention may be used to modulate biological pathways regulated or affected by nitric oxide.

Nitric oxide mediates vasodilation and can impact inflammatory responses, among other biological processes. Accordingly, diseases, disorders or conditions including conditions of interest in a subject or organ of a subject, or the blood of a subject, may be potentially treatable by administration of NO gas directly into ex vivo fluid according to the invention include respiratory, cardiovascular, pulmonary, and blood diseases, disorders or conditions, as well as hypoxemia, tumors, infections, inflammation, shock, ischemia reperfusion injury, sepsis and stroke. In specific examples, respiratory distress syndrome, asthma, bronchospastic disease, myocardial infarction, hemorrhage, sickle cell disease, platelet aggregation and major surgery may be treatable according to the methods of the invention. Further specific examples include pulmonary hypertension and hypoxemia following cardiopulmonary bypass, mitral valve replacement, heart or lung transplantation, and pulmonary embolism. The nitric oxide may also be used in ECMO circuits and/or in any aspect of the organ transplant process. Nitric oxide may also be used in cardiopulmonary bypass. Another example includes using nitric oxide to prevent and/or treat microcirculation alteration.

Administration of nitric oxide gas into ex vivo fluid may be useful in suppressing, killing, and inhibiting pathogenic cells, such as tumor/cancer cells, or microorganisms, including but not limited to pathogenic bacteria, pathogenic mycobacteria, pathogenic parasites, and pathogenic fungi. Examples of microorganisms include those associated with a respiratory infection within the respiratory tract.

Administration of nitric oxide gas into ex vivo fluids may enhance the survivability of biological materials, e.g., organs and tissues, that are subjected to ischemic or hypoxic conditions. In related embodiments, the present invention provides methods of preventing or reducing damage to biological materials, e.g., including cell, organ or tissue injuries resulting from ischemia or hypoxia. It is understood that a whole biological material or only a portion thereof, e.g., a particular organ, may be subjected to ischemic or hypoxic conditions.

The ischemic or hypoxic conditions may be the result of an injury or disease suffered by an organism. Examples of specific diseases that can induce ischemia or hypoxia include, but are not limited to, traumatic injury or surgery, respiratory or cardiac arrest, tumors, heart diseases, and neurological diseases. Examples of specific injuries that can result in ischemic or hypoxic conditions include, but are not limited to, external insults, such as burns, cutting wounds, amputations, gunshot wounds, or surgical trauma. In addition, injuries can also include internal insults, such as stroke or heart attack, which result in the acute reduction in circulation. Other injuries include reductions in circulation due to non-invasive stress, such as exposure to cold or radiation, or a planned reduction in circulation, e.g., during heart surgery.

In certain embodiments, methods of the present invention include administering NO-containing gas into ex vivo fluid prior to development of a disease, disorder or condition treatable with NO gas, e.g., prior to an ischemic or hypoxic injury or disease insult. Examples of such situations include, but are not limited to, major surgery where blood loss may occur spontaneously or as a result of a procedure, cardiopulmonary bypass in which oxygenation of the blood may be compromised or in which vascular delivery of blood may be reduced (as in the setting of coronary artery bypass graft (CABG) surgery), or in the treatment of organ donors prior to removal of donor organs for transport and transplantation into a recipient. Other examples include, but are not limited to, medical conditions in which a risk of injury or disease progression is inherent (e.g., in the context of unstable angina, following angioplasty, bleeding aneurysms, hemorrhagic strokes, following major trauma or blood loss).

In certain embodiments, methods of the present invention include administering NO-containing gas into ex vivo fluid after development or onset of a disease, disorder or condition treatable with NO, e.g., after an ischemic or hypoxic injury or disease insult, or after onset any of the diseases, disorders or conditions discussed above. In a particular aspect of such embodiments, NO-containing gas may be administered to a patient suffering from the disease, disorder or condition upon recognition or diagnosis of the disease, disorder or condition.

In certain embodiments, inflammatory-related diseases or disorders may be treated by administration of NO-containing gas directly into ex vivo fluid. Inflammatory-related diseases or disorders which may be treatable by the methods of the present invention include, e.g., multiple sclerosis, arthritis, rheumatoid arthritis, systemic lupus erythematosus, graft versus host disease, diabetes, psoriasis, progressive systemic sclerosis, scleroderma, acute coronary syndrome, Crohn's Disease, endometriosis, glomerulonephritis, myasthenia gravis, idiopathic pulmonary fibrosis, asthma, acute respiratory distress syndrome (ARDS), vasculitis, and inflammatory autoimmune myositis.

In one or more embodiments, the methods of the invention comprise administration of NO-containing gas directly into blood in an extracorporeal oxygenation system. The extracorporeal oxygenation system may be, for example, an extracorporeal membrane oxygenation (ECMO) system. In such methods the NO-containing gas is administered into the blood at any point in the ECMO circuit. In some embodiments, the NO is administered to arterialized blood, which is after oxygenation of the withdrawn blood. However, the NO may be administered in other points of the circuit, such as before oxygenation, or may be administered at multiple locations in the circuit. An exemplary ECMO circuit 100 according to the invention is illustrated in FIG. 1. Venous blood is withdrawn from the patient through venous cannula 105, which may be inserted in the right atrium, vena cava or femoral vein. Withdrawn venous blood is collected in reservoir 110 and circulated into membrane oxygenator 115 by pump 120. The membrane oxygenator removes $CO_2$ and oxygenates the blood before the blood is passed through heat exchanger 130. Oxygen is supplied to the membrane oxygenator 115 by oxygen source 117, which can be air, an oxygen blender, oxygen concentrator, or any other source of an oxygen-containing gas. The oxygenated blood is generally filtered through filter 135 prior to return to the body via arterial cannula 140, which may be inserted in the ascending aorta or the femoral artery. Alternatively, the cannula 140 may be a venous cannula for veno-venous (VV) ECMO. Heparin source 121 and fluid source 123 may be used to add anticoagulants and additional fluids, respectively, to the ECMO circuit. Non-heparin anticoagulants may also be used.

NO-containing gas may be introduced into the ECMO circuit via NO delivery device 145 which is in fluid communication with NO generating device/NO reservoir 150 and membrane oxygenator 115. NO-containing gas may be introduced into the ECMO circuit at any point in the circuit prior to return to the arterial circulation in the body. In the ECMO circuit illustrated in FIG. 1, this includes introduction before membrane oxygenator 115, in the membrane oxygenator 115, between oxygenator 115 and filter 135 or between filter 135 and arterial cannula 140. As shown in FIG. 1, NO may be administered in the membrane oxygenator 115 such that the NO and $O_2$ are administered at the same time, or the NO may be added in the membrane oxygenator 115 at any time after the blood is oxygenated. In some embodiments the NO is added shortly after the blood is oxygenated.

The pressure is measured in the ECMO circuit in at least two places, such as by first pressure sensor 155 and second pressure sensor 160. Pressure sensors 155 and 160 may be placed in various locations in the ECMO circuit, such as before and after the membrane oxygenator and any filter(s). The difference in pressure readings between pressure sensor 155 and pressure sensor 160 provides a pressure drop in the ECMO circuit. This pressure drop may become unacceptably high due to clogging, and thus nitric oxide administration may reduce the clogging and associated pressure drop by platelet deactivation.

In one or more embodiments, the pressure sensors 155 and 160 are in direct or indirect communication with the NO delivery device. The NO delivery device may compare the pressure sensor measurements from the two pressure sensors to determine a pressure drop in the ECMO circuit, or a separate component in the ECMO circuit may determine the pressure drop and communicate the pressure drop to the NO delivery device. The NO delivery device may compare the pressure drop to a pressure drop threshold and adjust the NO delivery based on this comparison. If the pressure drop meets or exceeds the pressure drop threshold, the NO delivery device may increase the NO delivery concentration to reduce clogging in the ECMO system. The target pressure drop in an ECMO circuit is typically 2-6%, but may vary between various ECMO circuits. Accordingly, the pressure drop threshold may be in the range from 1% to 30% relative to the maximum pressure in the ECMO circuit or relative to the higher reading between the two pressure sensors. Exemplary pressure drop thresholds include, but are not limited to, 1%, 1.5%, 2%, 2.5%, 3%, 3.5%, 4%, 4.5%, 5%, 5.5%, 6%, 7%, 8%, 9%, 10%, 15%, 20%, 25% and 30%.

In addition to administering NO to the blood, the NO delivery device may also monitor nitric oxide or a nitric oxide marker in the blood. Alternatively, the nitric oxide or nitric oxide marker may be monitored by a component separate from the NO delivery device.

The nitric oxide or nitric oxide marker may be monitored at any number of points within the ECMO circuit. Such locations include, but are not limited to, before oxygenation, after oxygenation and before NO administration, after NO administration but before re-introduction into the patient's circulatory system, and/or after re-introducing the blood into the patient's system. The nitric oxide or nitric oxide marker may be measured by sampling a portion of the blood from the circuit, such that a sample is removed from the circuit and analyzed. The sample size may be a very small amount. The nitric oxide or nitric oxide marker may also be measured directly in the blood circulating in the circuit. This can be accomplished by utilizing a capable sensor without removing blood from the circuit. For example, a pulse oximeter may be wrapped around the tube carrying the ex vivo blood or a probe may be placed in the blood flow. In the exemplary embodiment shown in FIG. 1, the nitric oxide marker is measured by the monitoring device 125 shortly before the ex vivo blood is re-introduced into the patient.

Figure 2:
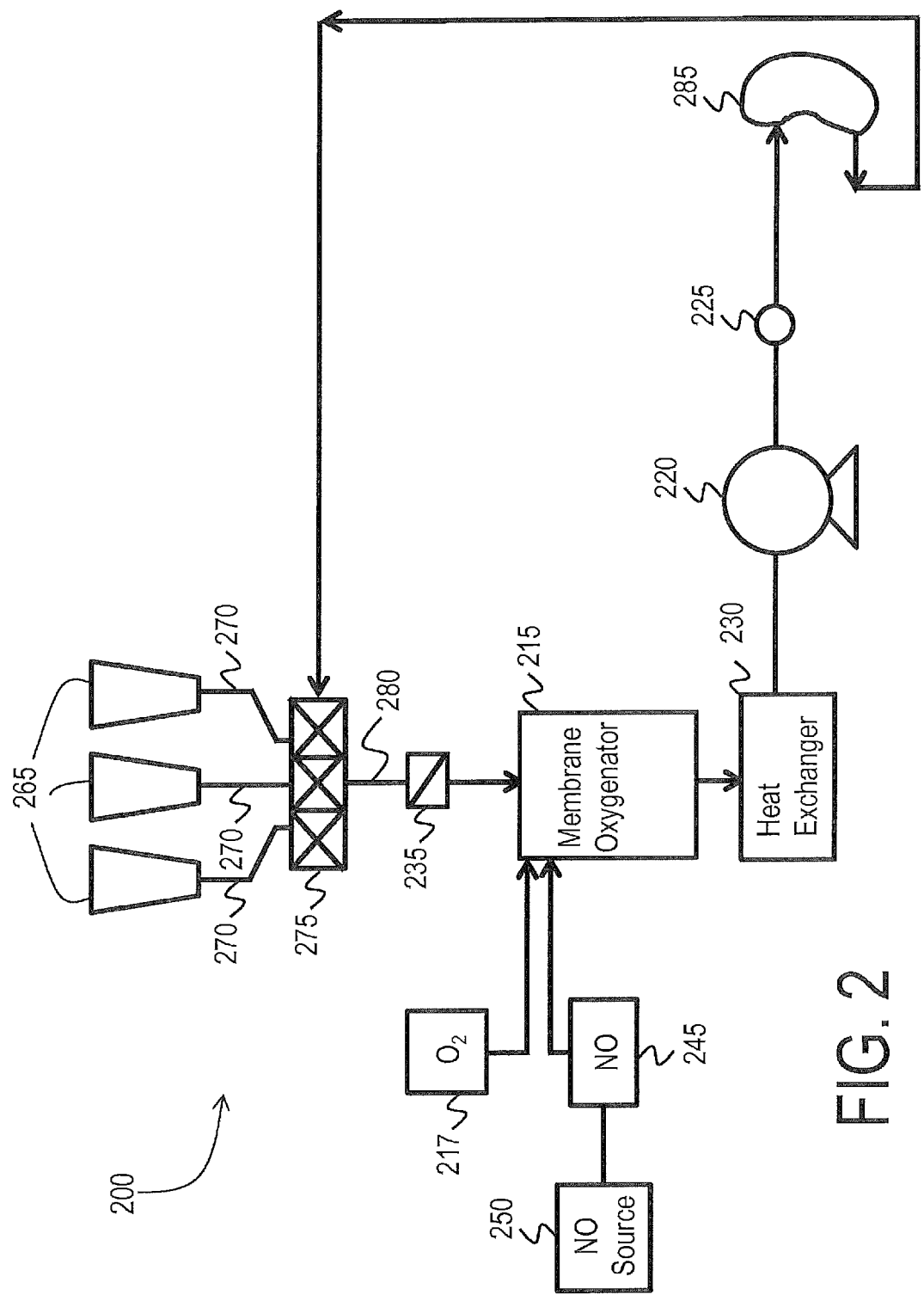
FIG. 2 illustrates an exemplary organ perfusion circuit that can be used in accordance with one or more embodiments of the invention.

Nitric oxide may also be administered and monitored in perfusion fluid for preserving organs or other biological material for transplant. FIG. 2 illustrates an exemplary organ perfusion circuit 200. One or more reservoirs 265 provide various components for the perfusion fluid. Each reservoir 265 is in fluid communication with a conduit 270 for carrying the respective components. A valve system 275 meters the components from the various conduits 270 to a common conduit 280 to provide the perfusion fluid for the perfusion circuit. As described above, the perfusion fluid may contain any known components, including red blood cells, salts, preservatives, etc. One or more filters 235 may be used before and/or after entering the membrane oxygenator 215. The membrane oxygenator 215 removes $CO_2$ and oxygenates the perfusion fluid. Oxygen is supplied to the membrane oxygenator 215 by oxygen source 217, which can be air, an oxygen blender, oxygen concentrator, or any other source of an oxygen-containing gas. The perfusion fluid may be warmed and/or cooled by one or more heat exchangers 230. A pump 220 provides the oxygenated perfusion fluid to the organ 290.

A NO delivery device 245 may be used to introduce NO-containing gas from a NO generating device/NO reservoir 250. NO-containing gas may be introduced into the organ perfusion circuit at any point in the circuit. In the organ perfusion circuit illustrated in FIG. 2, this includes introduction before the membrane oxygenator 215, in the membrane oxygenator 215, or between the membrane oxygenator 215 and organ 285.

The nitric oxide or nitric oxide marker may be monitored at any number of points within the perfusion circuit. Such locations include, but are not limited to one or more of, before oxygenation, after oxygenation and before NO administration, after NO administration but before exposure to the organ, and/or exposing the organ to the perfusion fluid. The nitric oxide or nitric oxide marker may be measured by sampling a portion of the perfusion fluid from the circuit, such that a sample is removed from the circuit and analyzed. The sample size may be a very small amount. The nitric oxide or nitric oxide marker may also be measured directly in the perfusion circulating in the circuit. This can be accomplished by utilizing a capable sensor without removing perfusion fluid from the circuit. In the exemplary embodiments shown in FIG. 2, monitoring device 225 measures the nitric oxide marker shortly before the perfusion fluid is delivered to the organ 285. A monitoring device may also comprise a probe placed in the perfusion fluid and/or organ that can provide real-time measurements of $NO_x$ levels, etc.

The organ perfusion circuit described herein can be utilized with any biological material in need of nitric oxide administration or in need of preventing and/or treating ischemia reperfusion injury. The biological material may include cells, tissue, or a partial or complete organ. The organs, tissue, and/or cells may be for any suitable type for transplant, including hearts, lungs, kidneys, livers pancreases, eyes, bones, skin, heart valves, bowels, tendons, ligaments or veins, or any portion or cells derived therefrom.

Different nitric oxide concentrations may be ideal for different organ types. The NO concentration can depend on many factors, including, but not limited to, the level of ischemia, amount of blood flow to the organ, NO tolerance of the organ, etc. For example, a heart other pulmonary organ may require more NO, whereas an organ that is sensitive to NO such as a brain may require less NO.

The timing and duration of NO delivery may also vary. The NO may be administered for the entire time that the organ is in the perfusion circuit, or may be administered for only a portion of the time. The start and end times for nitric oxide delivery may be within a given time period from when the organ is harvested from the donor, such as within 5, 10, 15, 20, 30, 45, 60 minutes or 1.5, 2, 2.5, 3, 3.5, 4, 5, 6, 7, 8 hours from when the organ is removed from the donor. The NO delivery may be performed within various time periods before cold ischemia prior to transplant, such as within 5, 10, 15, 20, 30, 45, 60 minutes or 1.5, 2, 2.5, 3, 3.5 or 4 hours prior to cold ischemia. The NO delivery may also be terminated within 5, 10, 15, 20, 30, 45, 60 minutes or 1.5, 2, 2.5, 3, 3.5 or 4 hours of transplant. The timing and duration of NO delivery may vary for individual organs.

In addition to administering NO to perfusion fluid, nitric oxide may be administered to either the organ donor and/or organ recipient to enhance the likelihood of success for the organ transplant. For example, it is believed that administration of inhaled nitric oxide (iNO) to the organ recipient will reduce primary graft dysfunction.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A method of monitoring nitric oxide administration to blood circulating in an extracorporeal oxygenation (ECMO) circuit for biological material preservation comprising: oxygenating the blood via a membrane oxygenator; administering nitric oxide to the oxygenated blood comprising red blood cells by contacting the blood with a gas comprising a nitric oxide delivery concentration in a range from 1 ppm to 300 ppm; monitoring, via a monitoring device, methemoglobin levels in the blood; decreasing the nitric oxide delivery concentration administered in a case where the methemoglobin levels meet or exceed 12% as a percentage of methemoglobin relative to the red blood cells.

2. The method of claim 1, wherein the biological material comprises one or more of isolated cells, tissue, a partial organ or a complete organ.

3. The method of claim 2, wherein the partial organ or the complete organ comprises one or more of a heart, lung, kidney, liver, pancreas, eye, bone, skin, heart valve, bowel, tendon, ligament or vein.

4. The method of claim 1, wherein decreasing the nitric oxide delivery concentration comprises adjusting the flow of the gas comprising nitric oxide.

5. A system for delivering and monitoring nitric oxide in blood circulating in an extracorporeal oxygenation (ECMO) circuit, the system comprising: a membrane oxygenator; a nitric oxide delivery device operably connected to the membrane oxygenator such that oxygen and nitric oxide from a nitric oxide source are administered to blood circulating in the ECMO circuit by contacting the blood with oxygen and a gas comprising a nitric oxide delivery concentration in a range from 1 ppm to 300 ppm; and a monitoring device for monitoring methemoglobin levels in the blood, wherein the monitoring device is in communication with the nitric oxide delivery device and the nitric oxide delivery device is configured to decrease the nitric oxide delivery concentration administered in a case where the methemoglobin levels meet or exceed 12% as a percentage of methemoglobin relative to the red blood cells.

6. The system of claim 5, wherein the monitoring device comprises one or more of a pulse oximeter or an optical measurement device.

7. The system of claim 5, wherein the nitric oxide delivery device is in communication with a first pressure sensor and a second pressure sensor in the extracorporeal oxygenation (ECMO) circuit that provide a first pressure reading and a second pressure reading, respectively, wherein the nitric oxide delivery device compares a differential between the first pressure reading and the second pressure reading to a pressure drop threshold, and wherein the nitric oxide delivery device adjusts, when the differential is equal to or greater than the pressure drop threshold, the nitric oxide administration based on the differential between the first pressure reading and the second pressure reading.

8. The system of claim 7, wherein the nitric oxide delivery device increases the nitric oxide administration it the differential between the first pressure reading and the second pressure reading is greater than 1% of the first pressure reading.

9. The system of claim 5, wherein the nitric oxide delivery device is further configured to adjust the flow rate of the gas comprising nitric oxide.

10. The system of claim 5, wherein the monitoring device is part of or integrated into the nitric oxide delivery device.

11. The system of claim 5, wherein the nitric oxide delivery device includes a pump, an injector, or a metering device.

12. The system of claim 5, wherein the gas comprising nitric oxide further comprises an inert diluent gas.

* * * * *